US00PP13651P29

(12) United States Plant Patent
Schlueter

(10) Patent No.: US PP13,651 P2
(45) Date of Patent: Mar. 11, 2003

(54) HIBISCUS ROSA-SINENSIS PLANT NAMED 'SATIN PILLOW'

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/153,117

(22) Filed: May 22, 2002

(51) Int. Cl.[7] ..... A01H 5/00
(52) U.S. Cl. ..... Plt./257

(58) Field of Search ..... Plt./257

*Primary Examiner*—Bruce R. Campell
*Assistant Examiner*—W C Haas
(74) *Attorney, Agent, or Firm*—Christie, Parker & Hale, LLP

(57) ABSTRACT

A new plant variety of *Hibiscus Rosa-sinensis* named 'SATIN PILLOW', characterized by a warm, satiny pink flower with a red "eye." The plant habit is upright and compact and is free-flowering. The foliage is glossy and dark green.

4 Drawing Sheets

BACKGROUND OF THE INVENTION

The present invention relates to a new and distinct variety of *Hibiscus Rosa-sinensis* L., which was developed in a controlled breeding program in Webster, Tex. by the originator Mr. Barry Schlueter. The varietal denomination of the new variety is 'SATIN PILLOW'.

The genus Hibiscus comprises about 250 species of herbs, shrubs and trees in warm temperate and tropical regions; with leaves usually simple, mostly palmately veined, lobed or parted; flowers mostly solitary in the leaf axils but sometimes in racemes, corymbs or panicles. Hibiscus is included in the family Malvaceae, which comprises about 95 genera of herbs, shrubs and trees originating in tropical and temperate regions. *Hibiscus Rosa-sinensis* is a glabrate shrub, seldom over 8 feet tall in cultivation, but treelike to 15 feet or more in tropical regions. Leaves to 6 inches long, ovate, usually serrate, mostly glossy green. Flowers solitary in upper leaf axils.

The new Hibiscus is a product of a planned breeding program conducted by the inventor in Webster, Tex. The objective of the program was to create new Hibiscus selections with improved bloom quality, color and floriferousness, plants that can be commercially produced on their own root systems, and improved plant habit with regard to vigor and post-production longevity.

SUMMARY OF THE INVENTION

The new variety was discovered in a controlled breeding program of *Hibiscus Rosa-sinensis* and differs from its parents and other known cultivars of *Hibiscus Rosa-sinensis* by the following characteristics in combination:

1. Upright, compact symmetrical plant habit that is suitable for container production;

2. Healthy green foliage;

3. Vigorous growth habit;

4. Large warm, satiny-pink flowers with a red "eye" or throat; and

5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER VARIETIES

'SATIN PILLOW' is distinguished from its female parent 'MISS LIBERTY' by its satiny pastel pink bloom with terrific sheen; 'MISS LIBERTY' is dark pink to light red with prominent white veining throughout the flower. 'SATIN PILLOW' is distinguished from its male parent 'MEDALLION' by its superior plant form; it is more upright and better branched than 'MEDALLION'. Plants of 'SATIN PILLOW' can be compared to plants of the cultivar 'SEMINOLE PINK', not patented. However, in side-by-side comparisons conducted in Webster, Tex., plants of the new cultivar differ from plants of the cultivar 'SEMINOLE PINK' in the following characteristics:

1. Flower color of 'SATIN PILLOW' is warmer than, and has a satiny sheen, as compared with are brighter in color than flowers of 'SEMINOLE PINK';

2. Plants of 'SATIN PILLOW' are more vigorous than those of 'SEMINOLE PINK'; and 3. Plants of 'SATIN PILLOW' possess healthier foliage than those of the cultivar 'SEMINOLE PINK'.

BRIEF DESCRIPTION OF ILLUSTRATIONS

The accompanying illustrations show a specimen of the new cultivar in a photographic illustration as true to color as is reasonably possible to make in an illustration of this character.

DESCRIPTION OF THE NEW VARIETY

Figure 1:
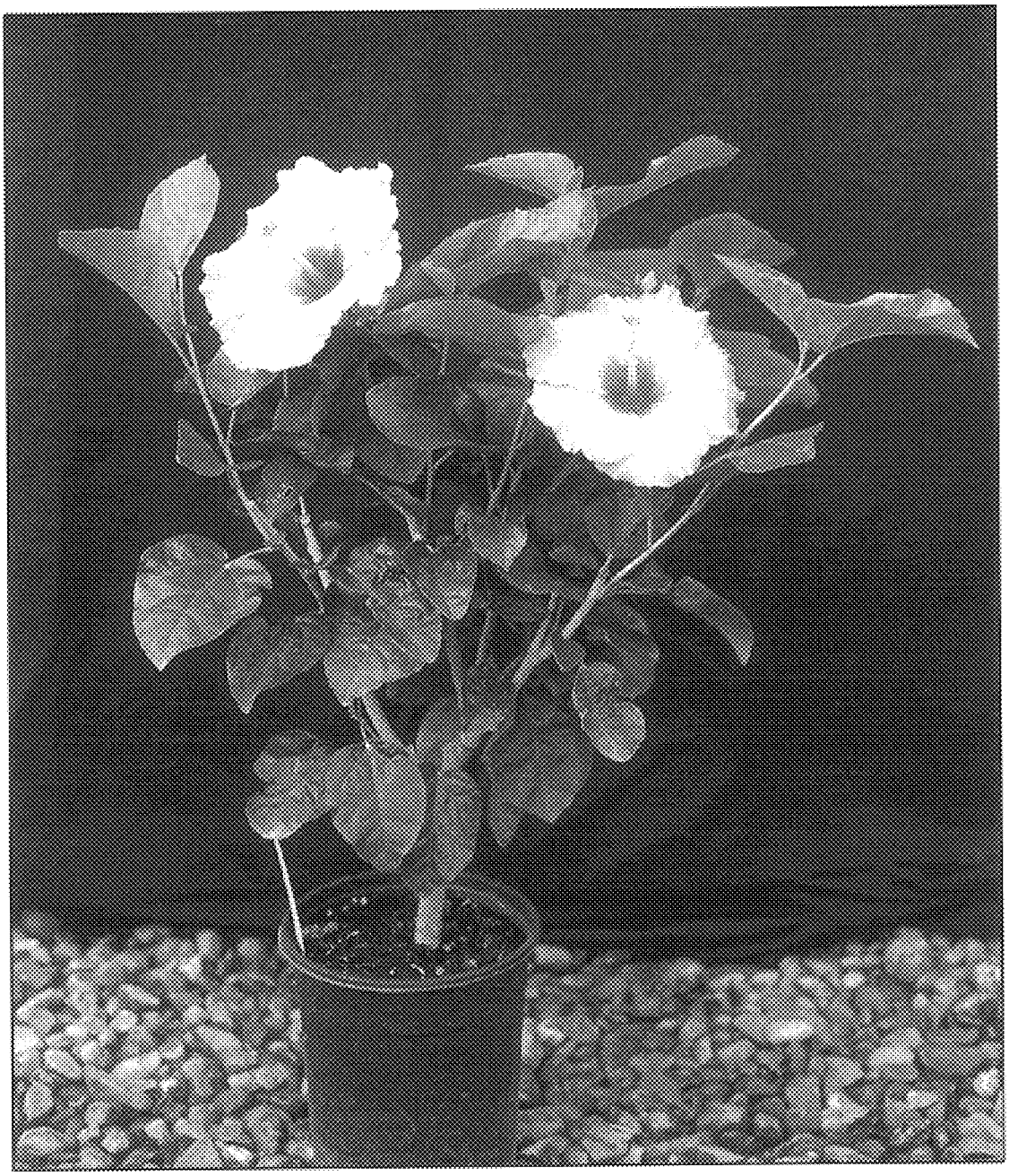
FIG. 1 illustrates a side perspective view of a typical plant of 'SATIN PILLOW'.
Figure 2:
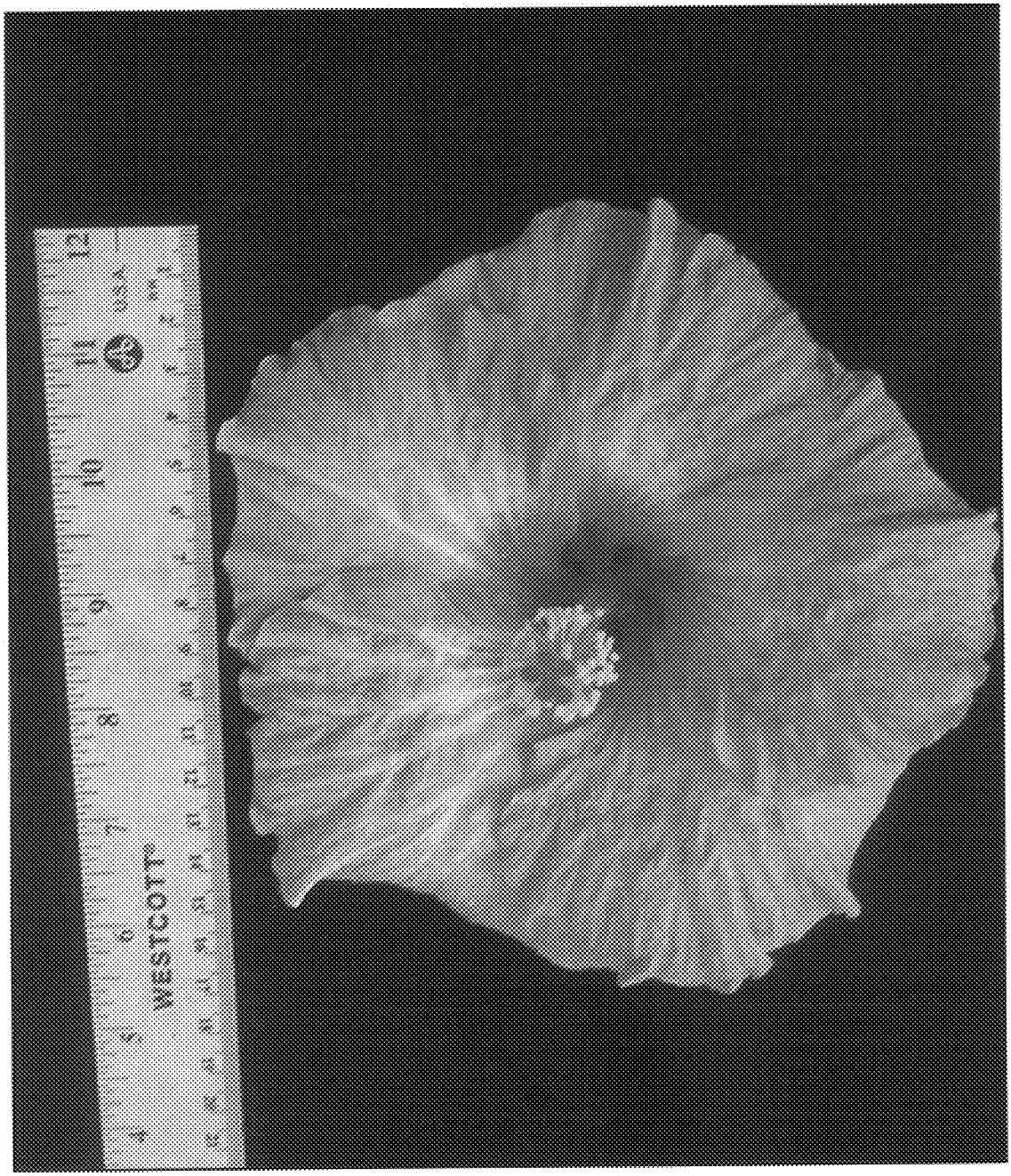
FIG. 2 illustrates the scale of a typical flower of 'SATIN PILLOW'.
Figure 3:
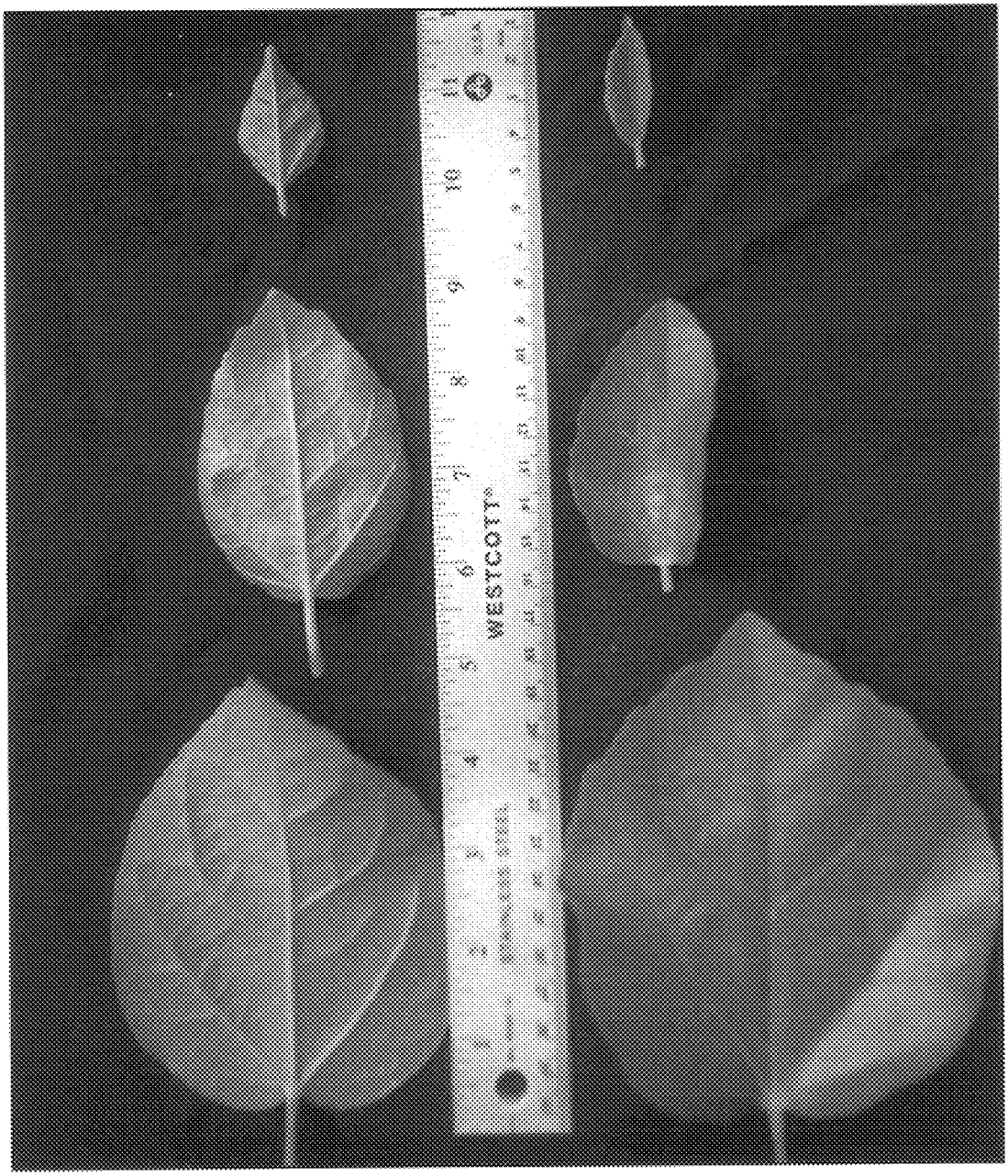
FIG. 3 illustrates the typical young to mature foliage of 'SATIN PILLOW'; the abaxial and adaxial surfaces are shown at each stage.
Figure 4:
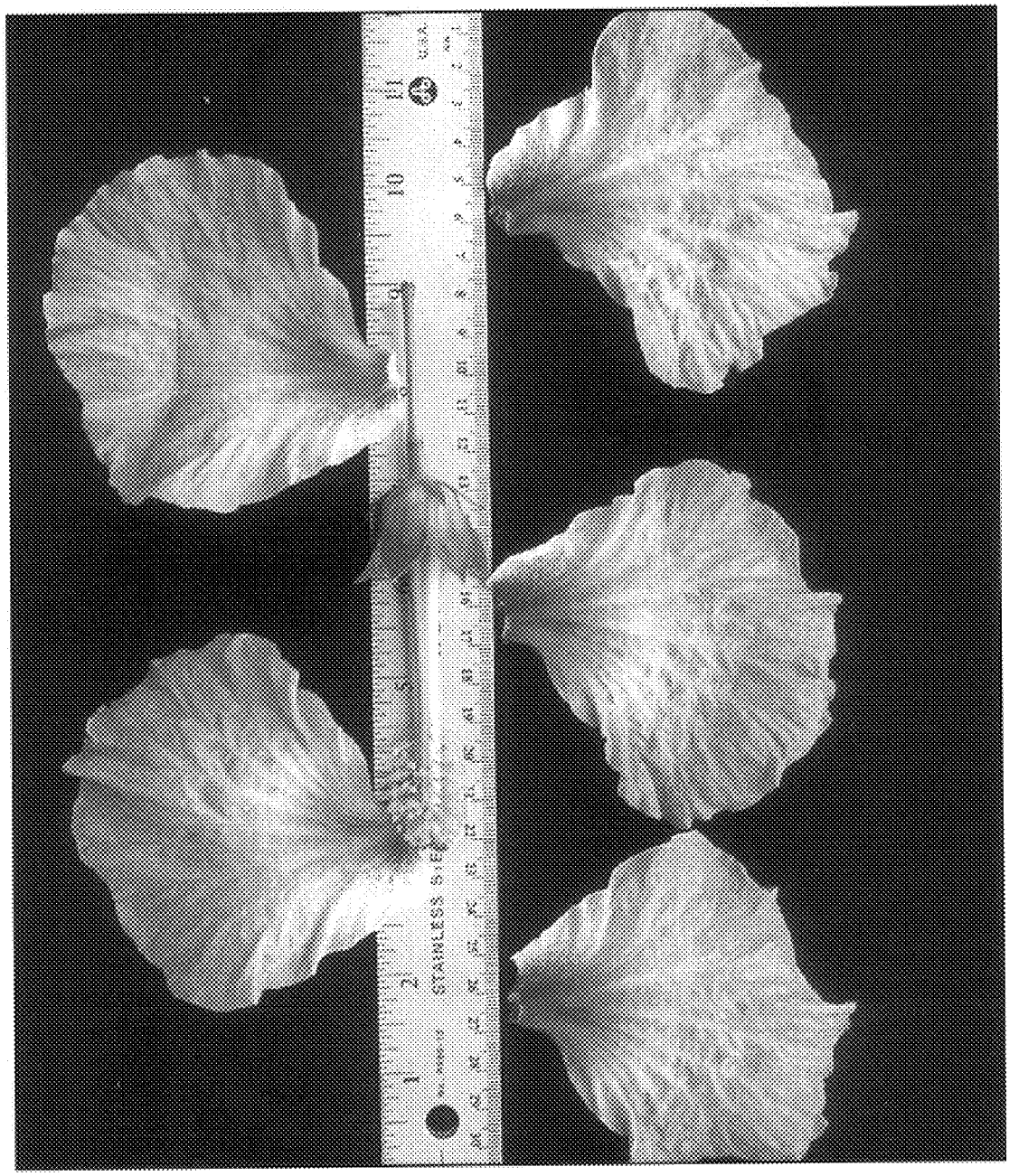
FIG. 4 illustrates a dissected flower of 'SATIN PILLOW', including shape and size of petals and characteristics of the reproductive structures.

'SATIN PILLOW' has not been observed under all possible environmental, cultural and light conditions. The following observations and descriptions are of plants grown in Fulshear, Tex., in October 2001, under polypropylene shadecloth providing a 30% light reduction, and under conditions which closely approximate commercial production. Plants described were approximately 1-year old and in a Number 3 nursery container.

In this description, color references are to The Royal Horticultural Society Colour Chart (1995) and terminology used in the color descriptions herein refers to plate numbers in this color chart. Phenotypic expression may vary with light intensity, cultural and environmental conditions.

CLASSIFICATION

Botanical: *Hibiscus Rosa-sinensis* L. 'SATIN PILLOW'.
Parentage:
- *Female.*—*Hibiscus Rosa-sinensis* 'MISS LIBERTY', not patented.
- *Male.*—*Hibiscus Rosa-sinensis* 'MEDALLION', not patented.

Propagation: By stem cuttings.
Time to initiate rooting: Approximately 14 to 21 days at 21° to 24° C.
Time to develop roots: Approximately 42 to 56 days at 21° to 24° C.
Root description: Fine to medium; fibrous; freely branching.

PLANT

Size:
- *Height.*—Approximately 55 cm from soil level to top of flowers.
- *Diameter/spread.*—Approximately 60 cm.

Form & growth habit: Perennial, evergreen shrub; mostly upright and somewhat spreading.
Branching: Freely branching; approximately 4 to 8 lateral branches develop after pinching.
- *Lateral branches.*—Approximately 20 cm long and 5 mm in diameter.
- *Internode length.*—Approximately 4 cm.

LEAF

Shape: Ovate.
- *Apex.*—Acute.
- *Base.*—Cordate.

Leaf size: Approximately 11 cm long and 10 cm wide.
Arrangement: Alternate, single; symmetrical.
Margin: Undulate with crenulate margins.
Aspect: Undulate.
Texture/substance: Glabrous, shiny.
Coloration:
- *Young foliage.*—Upper side: Near Green Group 137A to 137B. Underside: Near Green Group 138A.
- *Mature foliage.*—Upper side: Near Yellow-Green Group 147A. Underside: Near Yellow-Green Group 146B.

Petioles:
- *Size.*—Approximately 3 cm long, 3 mm across.
- *Coloration.*—Near Green Group 137C to 137D.
- *Texture.*—Smooth.

Hardiness: USDA Zone 10 (30° F. to 40° F.).
Pests/diseases: Resistance to known Hibiscus diseases had not been observed on plants grown under conditions approximating commercial practices.

INFLORESENCE

Bloom period: Typically year-round under subtropical and tropical conditions.
Flower arrangement: Arranged singly at terminal leaf axils; free-flowering with 3 to 4 flower buds and/or open flowers per terminal apex; flowers face upright and slightly outward.
Flower appearance: Ruffled pink petals with a red "eye" or throat; a white venation is present throughout the petals; flowers are open for about 2 days before closing; flowers persistent.
Flower size: Approximately 17 cm in diameter.

BUDS (JUST PRIOR TO SHOWING COLOR)

Rate of opening: Approximately 1 or 2 days, depending on temperature.
- *Shape.*—Elliptic.
- *Length.*—Approximately 2.8 cm.
- *Diameter.*—Approximately 1.6 cm.
- *Color.*—Near Yellow-Green Group 144A.

Fragrance: None.
Petals:
- *Number/arrangement.*—Corolla consists of 5 overlapping petals.
- *Shape.*—Spatulate with rounded apex.
- *Size.*—Approximately 10 cm long and 10 cm wide.
- *Margin.*—Entire, but ruffled.
- *Texture.*—Smooth.

Color:
- *Upper surface.*—The "eye" or throat is near Red Group 53B and the remainder of the petal is near Red Group 49A; the veins throughout the petals are near White Group 155A.
- *Lower surface.*—Near Red Group 49A; the veins throughout the petals are near White Group 155A.

Sepals:
- *Number/arrangement.*—5 sepals fused into a star-shaped calyx.
- *Shape.*—Linear with acuminate apices.
- *Margin.*—Entire.
- *Color.*—Near Yellow-Green Group 144A.

Peduncles:
- *Length.*—Approximately 4 cm.
- *Diameter.*—Approximately 3 mm.
- *Angle.*—Upright to about 45°.
- *Strength.*—Strong, flexible.
- *Color.*—Near Yellow-Green Group 146D.

REPRODUCTIVE ORGANS

Androecium:
- *Stamens.*—Numerous; about 52. Length: Approximately 5 mm. Filament Color: Near Red Group 48A.
- *Anther size.*—Approximately 1 mm.
- *Pollen amount.*—Abundant.
- *Pollen color.*—Yellow Group 10A.

Gynoecium:
- *Pistil length.*—8 cm.
- *Stigma appearance.*—5, rounded.
- *Stigma diameter.*—Approximately 4 mm.
- *Stigma color.*—Near Orange-Red Group 33A.

*Style color*.—Lower third near Red Group 53B; mid-third near Red Group 49B; upper-third near White Group 155B.

Seed production: Seed production has not been observed.

I claim:

1. A new plant variety of *Hibiscus Rosa-sinensis* of the variety substantially as shown and described.

* * * * *